United States Patent [19]
Li

[11] Patent Number: 5,211,477
[45] Date of Patent: May 18, 1993

[54] METHOD AND APPARATUS FOR SIMULTANEOUS DIFFERENTIAL SCANNING CALORIMETRY AND MICRODIELECTROMETRY

[75] Inventor: Chi Li, Orchard Lake, Mich.

[73] Assignee: Ford Motor Company, Dearborn, Mich.

[21] Appl. No.: 706,924

[22] Filed: May 29, 1999

[51] Int. Cl.$^5$ ................ G01K 17/00; G01R 27/21
[52] U.S. Cl. .................................. 374/33; 374/10; 324/686
[58] Field of Search .............. 374/10, 11, 12, 13, 374/33, 31, 43, 141; 324/663, 686, 690

[56] References Cited

U.S. PATENT DOCUMENTS

| | | | |
|---|---|---|---|
| 3,263,484 | 8/1966 | Watson et al. | 374/11 |
| 3,680,358 | 8/1972 | Takamatsu | 374/21 |
| 3,712,110 | 1/1973 | Paulik et al. | 374/12 |
| 3,798,003 | 3/1974 | Ensley et al. | 374/13 X |
| 4,112,734 | 9/1978 | Goryachev et al. | 374/11 |
| 4,423,371 | 12/1983 | Senturia et al. | |
| 4,777,431 | 10/1988 | Day et al. | 324/690 |
| 4,814,690 | 3/1989 | Melchor et al. | 324/663 |
| 4,848,921 | 7/1989 | Kunze | 374/11 |
| 4,861,167 | 8/1989 | Lobo et al. | 374/33 X |
| 4,892,707 | 1/1990 | Stockton et al. | 374/33 X |

FOREIGN PATENT DOCUMENTS

| | | | |
|---|---|---|---|
| 3226803 | 1/1984 | Fed. Rep. of Germany | 374/12 |
| 92942 | 6/1983 | Japan | 374/12 |
| 62-211566 | 9/1987 | Japan. | |

OTHER PUBLICATIONS

Tonkonogov et al., "Equipment for Measuring Electrical and Mechanical Properties of Dielectrics at Increased Temperatures", *Zavsdokaya Laboratories*, vol. 42, No. 10, pp. 1199-1201, Oct. 1976.

Baker, "Automatic Measurement Computation and Recording of Dielectric Constant and Loss Factor Against Temperature", *The Review of Scientific Instruments*, vol. 22, No. 6, Jun. 1951.

Primary Examiner—William A. Cuchlinski, Jr.
Assistant Examiner—G. Bradley Bennett
Attorney, Agent, or Firm—Joseph W. Malleck; Roger L. May

[57] ABSTRACT

A method and apparatus for simultaneous differential scanning calorimetry and microdielectrometry is disclosed. The apparatus includes a sample cell containing a sensor for measuring the dielectric and thermal properties of the sample. The method applies a voltage to a material while heating the material over a temperature range and then simultaneously measuring the current gain of the material, the temperature of the material and the energy input to the material.

15 Claims, 13 Drawing Sheets

METHOD AND APPARATUS FOR SIMULTANEOUS DIFFERENTIAL SCANNING CALORIMETRY AND MICRODIELECTROMETRY

BACKGROUND OF THE INVENTION

1. Field of the Invention

The present invention relates to a method and apparatus for simultaneously measuring the dielectric and thermal properties of a material. The present invention also relates to a specialized sample cell for performing these measurements.

2. Discussion of the Related Art

Thermoset polymers represent a very important class of materials for many types of manufacturing, including automotive. In automotive production, thermoset resins are used as induction- or oven-curable adhesives, reactive sealants, paints and primers, packaging and encapsulation resins for electric and electronic devices, structural composite components, composite body panels, etc. Thermoset materials, once properly cured, provide superior dimensional stability due to the chemical crosslinks in their molecular structure. Since the extent of cure of the crosslinked polymers is one of the most important factors in governing the performance of the final products, the cure of thermoset materials have been studied extensively by both theoretical and experimental means. Dielectric measurements have been applied to the studies of curing of thermoset materials because such measurements can be carried out through the curing cycle from liquid resin to highly crosslinked solid. Recent technological developments in microelectronics have made silicon-chip based interdigitated comb electrodes available for microdielectrometry. Microdielectrometry provides a sensitive and convenient way of measuring molecular and ionic mobility in liquid resins or solid polymers. It is known that the progress of curing reaction of thermoset resins can be monitored by microdielectrometry. Microdielectrometry, however, provides only a relative measure of cure of a given commercial resin. An absolute characterization of cure requires the use of additional experimental methods which have previously been performed at a different time.

Differential Scanning Calorimetry (DSC) provides quantitative measurements of the instantaneous heat capacities and thermal events of polymer liquids or solids. Thus, DSC is an ideal method for quantifying the amount of heat being released during the highly exothermic polymerization reactions of thermoset polymers. DSC has also been applied to study quantitatively the cure kinetics of thermoset resins. The extent of curing reaction can be readily calculated by normalizing the amount of heat released from a reacting resin at a given condition to the total heat of reaction. The temperature control in a DSC chamber is superior to that of many programmable ovens, and thus, precisely controlled cure schedules can be achieved. DSC, however, does not allow in-situ measurement of cure for industrial applications. Furthermore, DSC cannot measure diffusion process of thermoplastic plastisols commonly used as a component in industrial adhesives and sealers.

SUMMARY OF THE INVENTION

The present invention has discovered that by combining microdielectrometry and DSC measurements from the same sampling cell, the correlation between the dielectric response and the extent of reaction in a thermoset resin can be investigated. Once such a relationship is established, microdielectrometry provides a convenient method of in-situ cure monitoring for research, product development, or process modeling.

An object of the present invention is to develop an experimental method to measure simultaneously the thermal properties (e.g. heat of reaction, $\Delta H_r$, glass transition temperature $T_g$) and the frequency dependent dielectric response (primarily dielectric constant $\epsilon'$, and dielectric loss $\epsilon''$) of thermoset resins.

Another object of the present invention is provide a device capable of simultaneously measuring the thermal properties and dielectric properties of a material.

A further object of the present invention is to provide a sample cell which includes a sensor whereby a material can be simultaneously measured for its thermal and dielectric properties.

The above and other objects of the present invention are accomplished by a method which applies a voltage to a material while heating the material over a temperature range and then simultaneously measuring the current gain of the material, the temperature of the material and the energy input to the material.

The above and other objects of the present invention are also accomplished by a device which includes a sample cell and associated electronics for simultaneously measuring dielectric and thermal properties of a material.

BRIEF DESCRIPTION OF THE DRAWINGS

The invention will now be described further, by way of example, with reference to the accompanying drawings, in which.

DETAILED DESCRIPTION OF THE PREFERRED EMBODIMENTS

Figure 1:
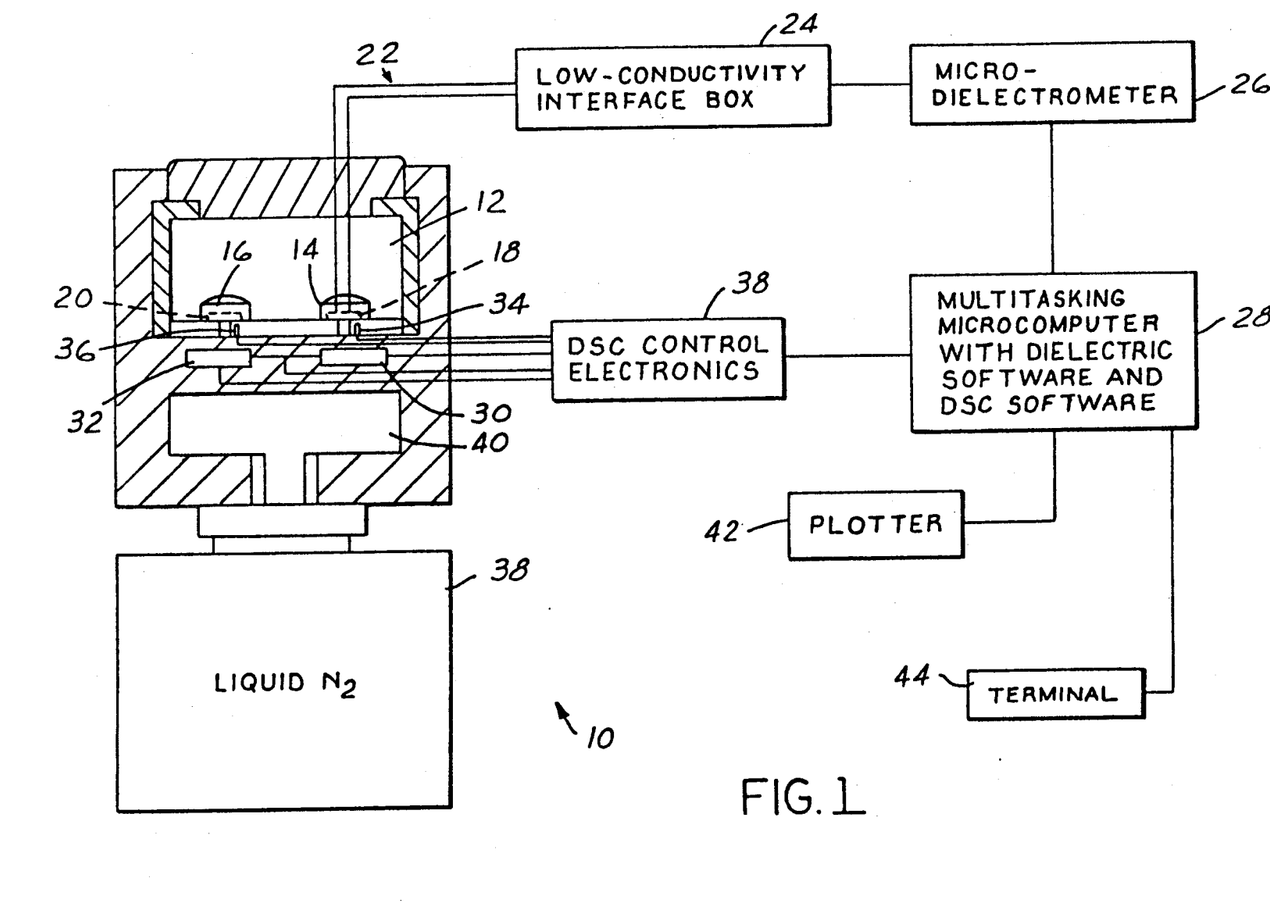
FIG. 1 is a schematic view of the device for simultaneous differential scanning calorimetry and microdielectrometry measurement according to the present invention.

FIG. 1 discloses a schematic view of the present invention for simultaneous differential scanning calorimetry and microdielectrometry measurements. The overall device illustrated by reference numeral 10. The device 10 includes a chamber 12 into which are placed sample cell 14 and reference cell 16. Each of the cells 14 and 16 contain a sensor 18 and 20. The sensor 18 disposed in the sample cell 14 will be described later in detail with reference to FIGS. 2-4. As can be seen from FIG. 1, the sensor 18 is connected via Kapton insulated ribbon cable 22 to low conductivity interface box 24, which is in turn connected to a microdielectrometer 26 which feeds information to a multitasking microcomputer 28. Below the sample cells 14 and 16 are located heating elements 30 and 32. Temperature probes 34 and 36 are disposed adjacent to the sample in reference cells 14 and 16 for sensing the temperature of each cell. The heating elements 30 and 32 and the temperature probe 34 and 36 are connected to DSC control electronics 38 by cables. The temperature probes 34 and 36 provide information to the control electronics 38 via a feedback loop for providing information so that the heating elements 30 and 32 can be regulated to maintain the sample cells 14 and 16 at a constant temperature over the temperature range in which they are heated.

The device also includes a liquid nitrogen storage tank 70 which supplies liquid nitrogen to a liquid nitrogen chamber 40 as is well known in the art of a differential scanning calorimetry.

The DSC control electronics 38 supply the microcomputer 28 with the necessary information for calculating the instantaneous heat capacities and other properties measured by the differential scanning calorimetry. Thus, the multitasking microcomputer 28 can calculate the results of the simultaneous microdielectrometry measurements and differential scanning calorimetry measurements and either output the results to a plotter 42 or to a terminal 44. The terminal 44 also acts as an input device for inputting information specific to each test run such as the temperature ramping scale which is desired for differential scanning calorimetry.

While FIG. 1 has been shown with a multitasking computer 28 doing both the computations for the dielectric microdielectrometry and differential scanning calorimetry, it is possible to have two separate microcomputers which can do this job. One microcomputer could do the computations for the microdielectrometry measurements and the other microcomputer could be programmed to do the differential scanning calorimetry measurements. This information then could be coordinated in a single computer and then printed on a plotter such as that described by reference numeral 42.

Figure 2:
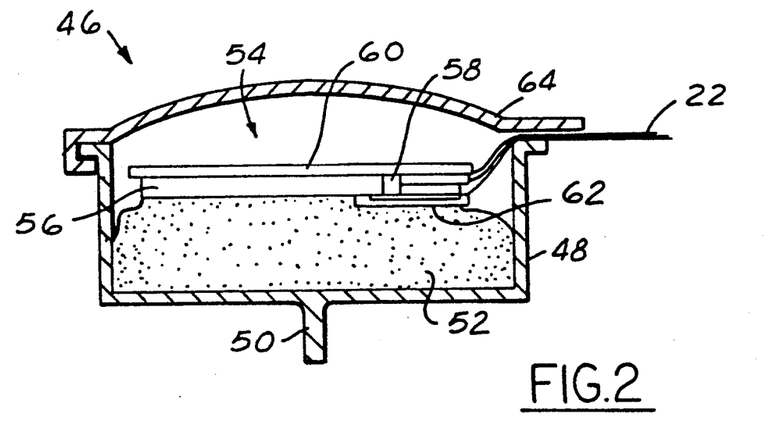
FIG. 2 is a detailed cross sectional view of a first embodiment of a sample cell used in the device shown in FIG. 1 according to the present invention.

FIG. 2 discloses a cross-sectional schematic view of a sample cell for simultaneous differential scanning calorimetry and microdielectrometry measurement illustrated as reference numeral 46. The sample cell 46 includes a sample pan 48 which can be made of aluminum or copper. The sample pan 48 may include a centering pin 50 for positioning the sample cell in the testing device of chamber 12. Disposed in the sample pan 48 is a sample 52 of a material to be analyzed. On top of the sample is a microdielectrometry sensor 54. The sensor 54 is comprised of a silicon chip 56. Adjacent the silicon chip 56 is a low-conductivity microchip sensor 58 and above the sensor and silicon chip is a layer of Kevlar 60. The bottom surface of the microchip sensor 58 is also protected by a layer of Kevlar 62. Information is relayed back to the low conductivity interface box 24 by the cable 22 shown in FIG. 2.

As can be seen from the arrangement in FIG. 2, the sensor is disposed above the sample so that the sensing area is located on the bottom of the microdielectrometry sensor 54. Once the sensor 54 has been installed into the sample pan of 48 on top of the sample 52, a sample Pan cover 64 is placed on top of the sample pan and its edges are crimped over the edges of the sample pan except in the region where the cable 22 exits the sample cell 46.

Figure 3:
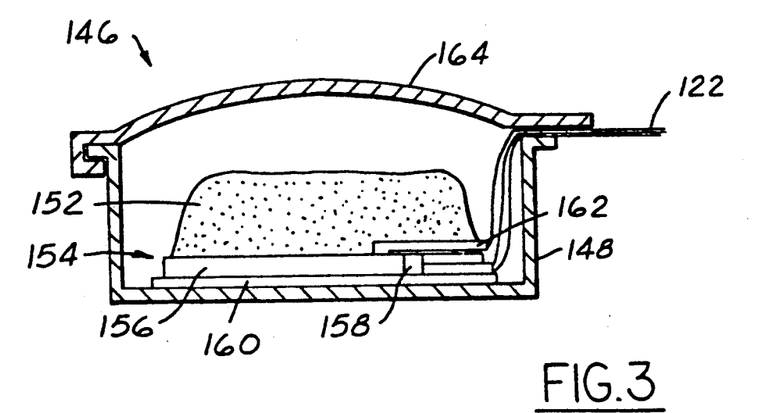
FIG. 3 is a detailed cross sectional view of a second embodiment of a sample cell used in the device shown in FIG. 1 according to the present invention.

FIG. 3 discloses a second embodiment of a sample cell wherein the reference numerals used are the same as FIG. 2 except that they are prefaced by the numeral 1.

FIG. 3 discloses a sample cell 146 having a sample pan 148. Disposed in bottom of the sample pan is a microdielectrometry sensor 154. The sensor 154 includes the silicon chip 156, the low conductivity microchip sensor 158 and Kevlar protection pieces 160 and 162. The information is fed back to the microdielectrometer via cable 122 which exits the side between the sample pan 148 and the sample pan cover 164. Disposed on top of the microdielectrometry sensor 154 is a sample 152 of material to be analyzed. In this embodiment it is noted that the sensoring pin is not shown; however, it is possible that a centering pin could also be added to this arrangement.

Figure 4:
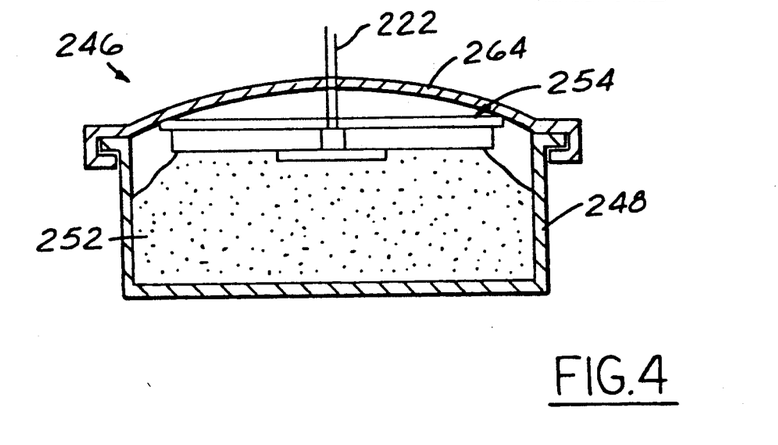
FIG. 4 is a detailed cross sectional view of a third embodiment of a sample cell used in the device shown in FIG. 1 according to the present invention.

FIG. 4 discloses a third embodiment of a sample cell wherein the reference numerals used are the same as FIG. 2 except that they are prefaced by the numeral 2. In FIG. 4 the sample cell 246 is disclosed which includes a sample pan 248 containing a sample of material 252 therein. Disposed above the sample 252 is a microdielectrometer sensor 254. In this embodiment the cable 222 comes out the top of the sample cell 246 through the cover 264. This arrangement is similar to that shown in FIG. 2 with the exception that the cable is disposed through the cover. This allows the edges of the cover to be crimped completely around the flange of the pan, thereby insuring a tight seal.

Once the particular sample cell arrangement is chosen and the sample is installed into the sample cell, the testing of the particular material selected may begin. In this operation the differential scanning calorimetry and microdielectrometry measurements are taken over a temperature range of $-100°$ C. to $250°$ C. Above $250°$ C. the sensor for measuring the microdielectrometry properties can become unreliable.

One of ordinary skill in the art will be familiar with the experimental procedures and measurements which may be obtained using either differential scanning calorimetry or microdielectrometry. With this background the specific examples studied will now be described.

Examples of two epoxy based adhesives, a commercial material and a model material, are given below. Both isothermal and non-isothermal cure schedules were studied. The correlation between DSC and dielectric response was obtained by real-time isothermal experiments. Attempts have also made to analyze the relationship between the dielectric properties and the extent of reactions using the data collected in the simultaneous experiments.

EXAMPLES

Two thermoset resins were examined: a commercial one-component epoxy resin (Terokal-3919-US, supplied by W.R. Grace Company) and a model one-component epoxy resin based on epoxy-dicyandiamide chemistry. The model epoxy resin, designated as ER-1, is prepared by mixing 84 wt. % Epon-828 (from Shell Oil Company), 6 wt. % dicyandiamide (from Aldrich Chemical Company), and 10 wt. % fumed silica filler (from Carbot). The commercial one-component epoxy resin, designated as ER-2, is also formulated by using the typical epoxy-dicyandiamide chemistry in addition to an acrylic thermoplastic component. Both epoxy resins were stored in a vacuum chamber at about 0.1 torr at room temperature prior to DSC-Microdielectrometry experiments.

The sampling cell for simultaneous DSC-Microdielectrometry is prepared by embedding the silicon-chip-based low-conductivity sensor, supplied by Micromet Instrument, Inc., into a Mettler DSC pan. The Micromet low conductivity chip sensor consists of an interdigitated comb electrode for dielectric measurement, a pre-amplifier for eliminating stray capacitance, and a thermal diode for temperature measurement. The Kapton ribbon packing area on three sides of the sensor chip was cut off for size reduction; thus, the sensor could be embedded in the DSC pan containing about 25 to 35 mg of the epoxy resin. After inserting the sensor, the DSC pan was sealed with an aluminum lid. Another chip sensor, cut off from the Kapton cable, was embedded in an empty DSC pan to serve as the reference cell for the DSC. The sampling cell and the reference cell were then placed in the DSC chamber. The Kapton-encapsulated cable from the sampling cell was connected to the low-conductivity interface box of the microdielectrometer.

The instrumentation for simultaneous DSC-Microdielectrometry consisted of a Mettler TA-3000 DSC device connected to an IBM-PC/AT microcomputer and Eumetric System II Microdielectrometer controlled by another IBM-PC/AT with the Eumetric dielectric analysis software. The DSC was operated by its own microprocessor-based control station and the microcomputer serves only as a data storage and analysis unit. Mettler TA-70 data analysis software was used for analysis of the DSC results ($T_g$ calculation, peak area integration, etc.). FIG. 1 illustrates the instrument system for simultaneous DSC-Microdielectrometry. Software developed in-house was used to convert both the DSC and the dielectric data files into ASCII format so that the data could be plotted using standard graphics software. Graphical presentation of the results of the simultaneous experiments was achieved by plotting the DSC and the dielectric data versus a common variable: time or temperature. The dielectric measurements and the DSC heat flow measurements for a given experiment were synchronized by activating the data acquisition programs at the same time. The frequencies of dielectric measurements were selected at 1.0, 2.0, 3.0, 5.0, and 10.0 kHz.

Isothermal and temperature-scan experiments were carried out using the simultaneous DSC-Microdielectrometry systems. The Mettler DSC is based on the heat flow principle, so the thermal lag of the sampling cell must be estimated and corrected. The heat transfer between the DSC heating element and the sampling cell was examined at different scanning rates by using the thermal diode (temperature probe) on the dielectric sensor. At 5° C./min or lower DSC scanning rates, the temperature difference between the DSC heating element and the dielectric sensor inside the DSC pan did not exceed 0.2° C., indicating a minimum thermal lag of the sampling cell at low scan rates. Thus, the temperature-scan experiments were carried out at a 3° C./min rate. In the isothermal experiments, the sampling cell in the DSC was heated at 50° C./min to the designated temperature and the heat flow to the cell was measured at the specified temperature. The temperature inside the sampling cell was measured using the thermal diode.

The extent of curing action, $\alpha$, of each thermoset resin is determined by dividing the heat of reaction at a given time $\Delta H(t)$, by the total heat of reaction $\Delta H$, determined from a DSC scan: $\alpha(t) = \Delta H(t)/\Delta H$.

The spacing between two adjacent electrodes is 20 $\mu$m which is also the sampling depth of the silicon chip sensor. Complete coverage of the sensing area with a proper amount (35 to 40 mg) of sample in the cell is very important to ensure good signal to noise ratio in the simultaneous measurements.

Figure 5:
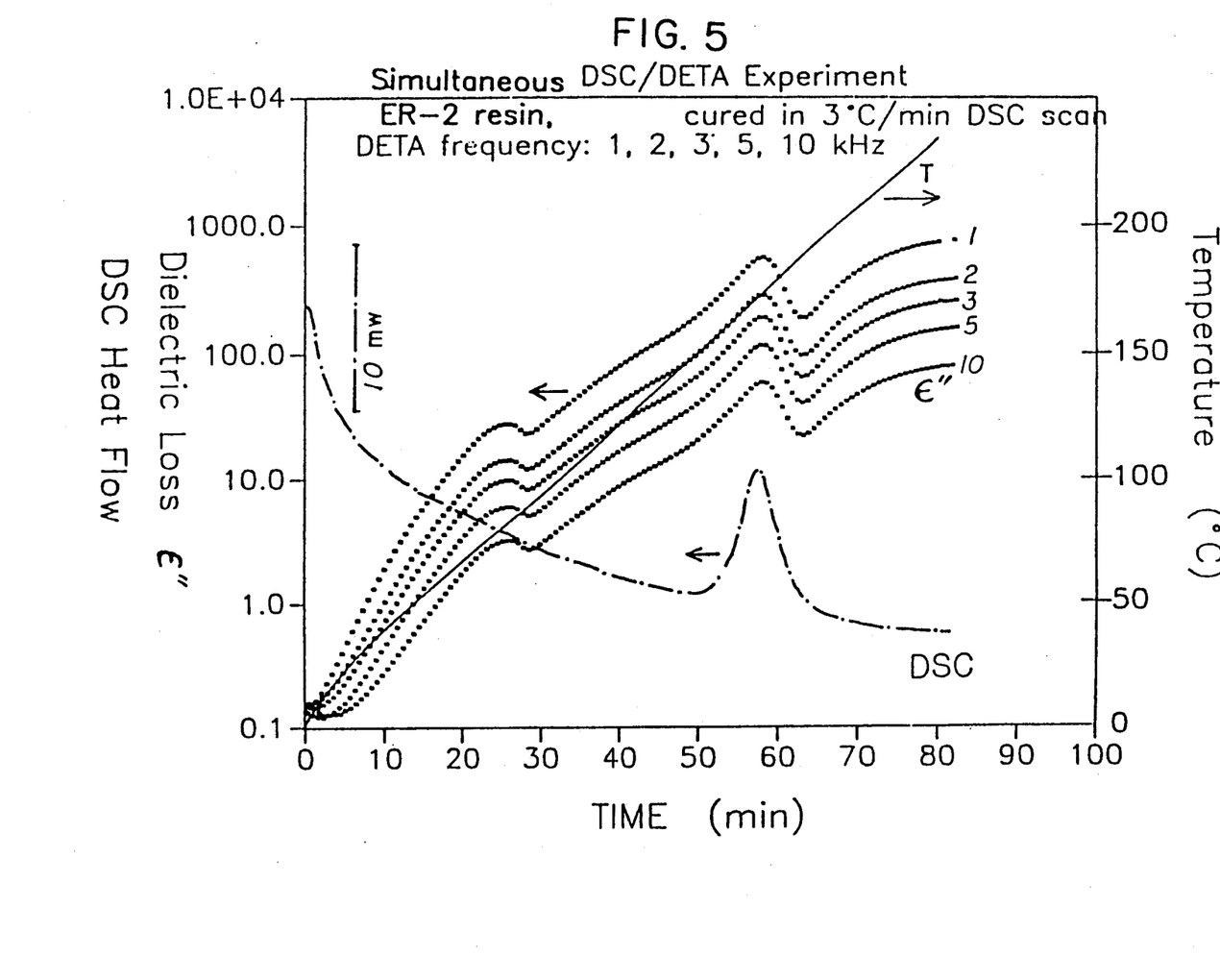
FIG. 5 is a graph showing the dielectric loss, DSC heat flow, and cell temperature as functions of scanning time measured in a simultaneous DSC-Microdielectric experiment of curing the ER-2 resin at a 3° C./min scan rate.

FIG. 5 illustrates the dielectric loss, $\epsilon''$, measured at 1, 2, 3, 5, and 10 kHz excitation frequencies, the DSC heat flow, $dC_p/dt$, and the cell temperature, T, as functions of scan time, t, recorded in a simultaneous DSC-Microdielectrometry experiment of the ER-2 resin in a 3.0° C./min scan from 0° C./min scan from 0° C. to 250° C. The DSC curve shows an exothermic peak at 58 min (181° C.) typical of the curing reaction of epoxy-dicyandiamide system. The $\epsilon''$ curves show two phenomena; a decrease of dielectric loss at all frequencies at 27 min (79° C.) due to the fusion of an acrylic thermoplastic component in this resin, and a greater decrease of dielectric loss at all frequencies at 58 min (181° C.) due to the epoxy-dicyandiamide crosslinking reaction.

The fusion of the thermoplastic particles in the ER-2 resin at 27 min (79° C.) is not reflected in the DSC heat flow curve because the phenomenon is not accompanied by a noticeable change in thermal property. The fusion process, however, solidifies the viscous paste of ER-2 to a low-modulus gel by forming a compatible blend of epoxy monomer with acrylic thermoplastic polymer. The decrease in dielectric loss $\epsilon''$ observed during the solidification of ER-2 is attributed to a significant decrease in the molecular motion of the resin associated with the change of its aggregation state.

Increased ionic conduction in the low-modulus gel of ER-2 resin at higher temperatures was reflected by the monotonic increase of dielectric loss, $\epsilon''$, from 32 min (90° C.) to 58 min (181° C.). The additional evidence for ionic conduction in this temperature range is that at a given temperature the dielectric loss, $\epsilon''$, is inversely proportional to the excitation frequency, shown in FIG. 6. When the sampling cell is heated above 150/° C. (50 min), the exothermic curing reaction of epoxy-dicyandiamide take place as indicated by the onset of the exothermic peak measured from DSC. The DSC exotherm peaks at 181° C. (58 Min). A rapid increase in dielectric loss can be seen in each $\epsilon''$ curve from 50 min (152° C.) to 58 min (181° C.) due to the increase of cell temperature associated with the exothermic reaction. The subsequent decrease of dielectric loss, $\epsilon''$, due to the increase of crosslink density in the resin is observed from 58 min (181° C.) to 67 min (201° C.). The dielectric loss, $\epsilon''$, increases again with temperature after the completion of the curing reaction due to a high ionic conductivity at high temperatures.

Figure 6:
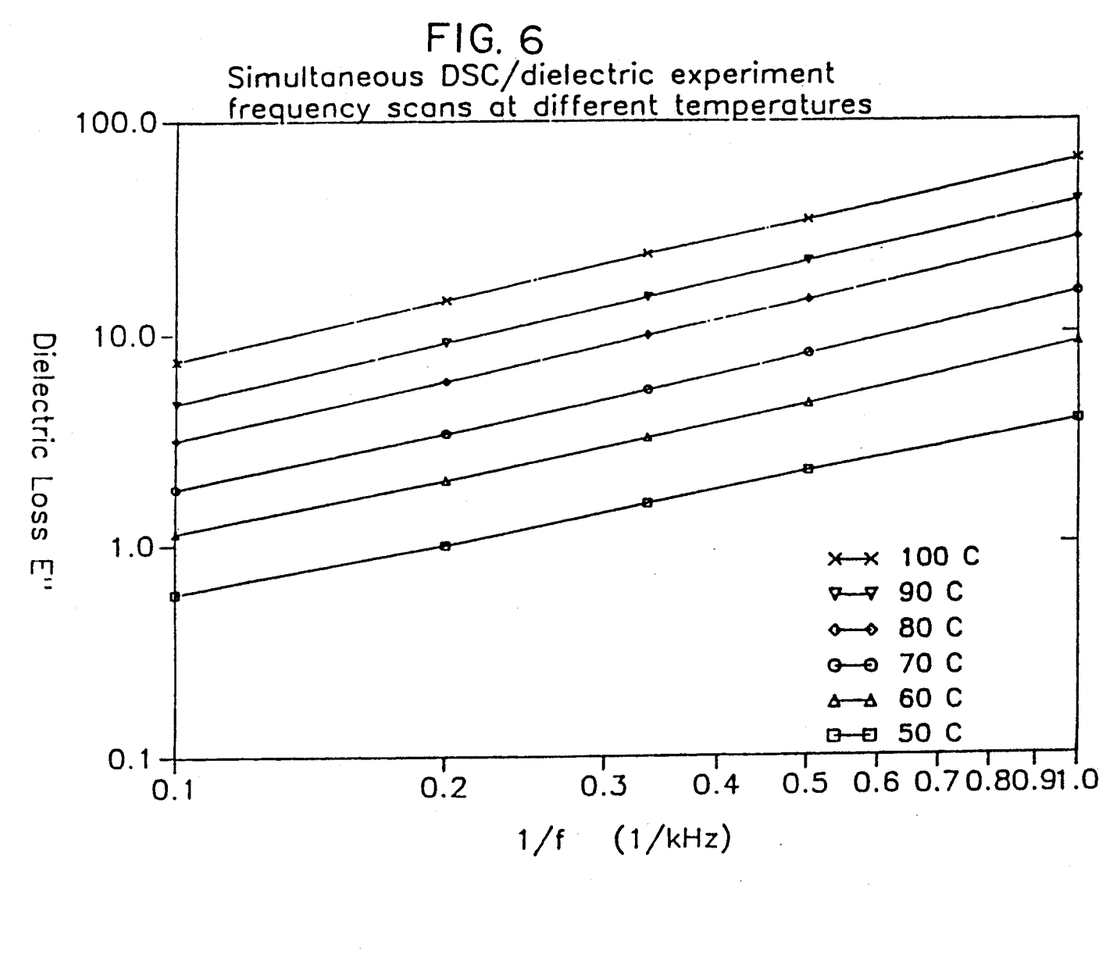
FIG. 6 is a graph showing dielectric loss of the ER-2 resin as a function of excitation frequency measured from 50° C. to 100° C.
Figure 7:
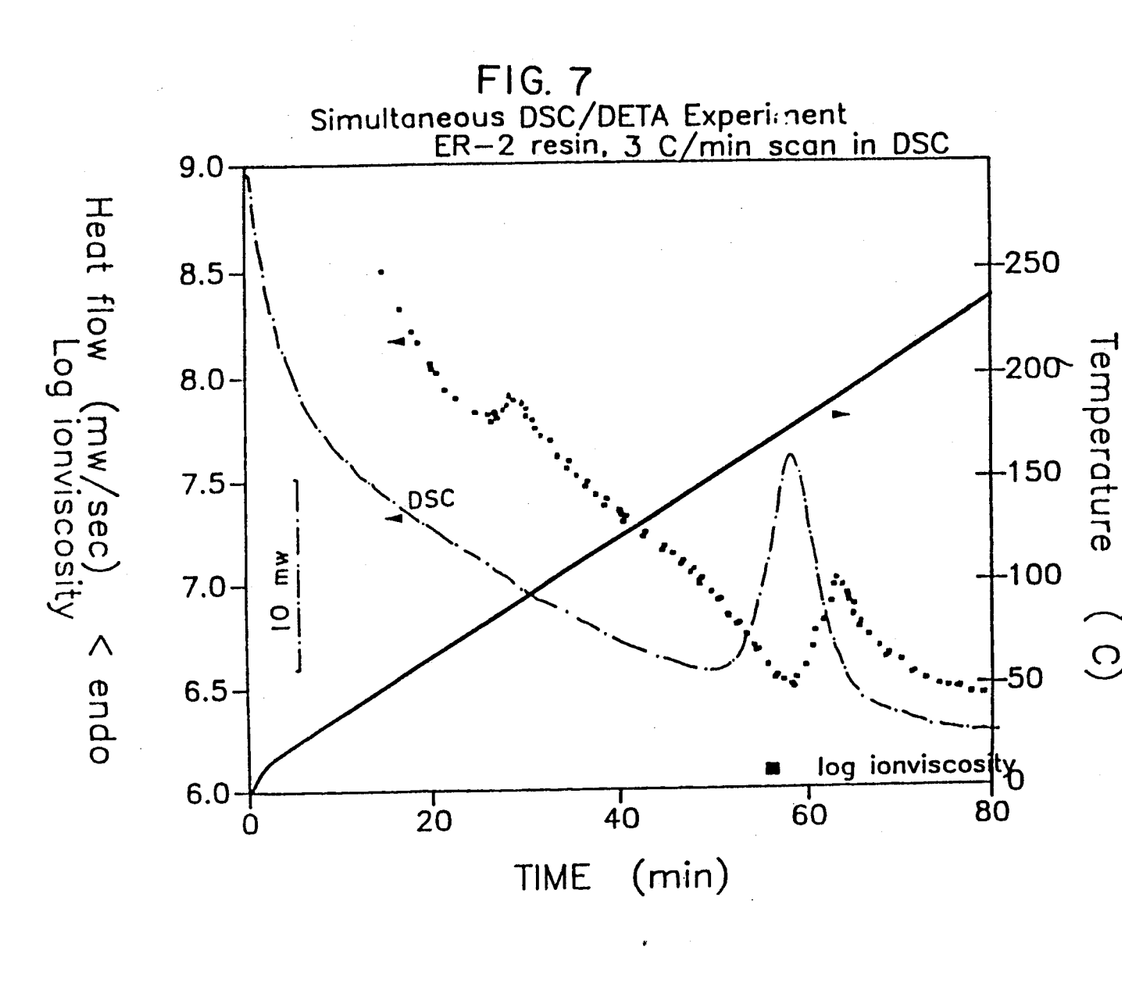
FIG. 7 is a graph showing ionic viscosity and DSC heat flow as functions of cell temperature of the ER-2 resin cured in a 3° C./min temperature scan.

The ionic viscosity, $\eta_i$, and the DSC heat flow, $dC_p/dt$, are plotted vs. cell temperature in FIG. 7 to illustrate the relationship between the dielectric and DSC response with respect to the extent of cure of ER-2 resin. Since the dielectric loss due to ionic conduction is inversely proportional to the excitation frequency as shown in FIG. 6, the ionic viscosity, $\eta_i$, proportional to $\frac{1}{2}\pi f \epsilon''_i$, should be independent of the excitation frequency. It is seen in FIG. 7 that the calculated ionic viscosity does not show frequency dependence, confirming that, in the temperature range of the experiment, the dipolar component of the dielectric loss is negligible, i.e. $\epsilon'' \simeq \epsilon''_i$. The high level of ionic conductivity in this resin can be attributed to a high concentration of ionic additives and impurities in the material. FIG. 7 also shows the change of the ionic viscosity due to a change in the physical state of the resin; an increase of $\eta_i$ at 79° C. due to the fusion of the acrylic thermoplastic particles and a large increase of $\eta_i$ at 172° C. due to the epoxy-dicyandiamide curing reaction. Compared to the DSC exotherm peaked at 181° C., the ionic viscosity shows a delayed response because the increase of ionic (local) viscosity takes place in the late stage of cure. Therefore, the measurement of ionic viscosity provides a more sensitive determination of the end point of cure.

Figure 8:
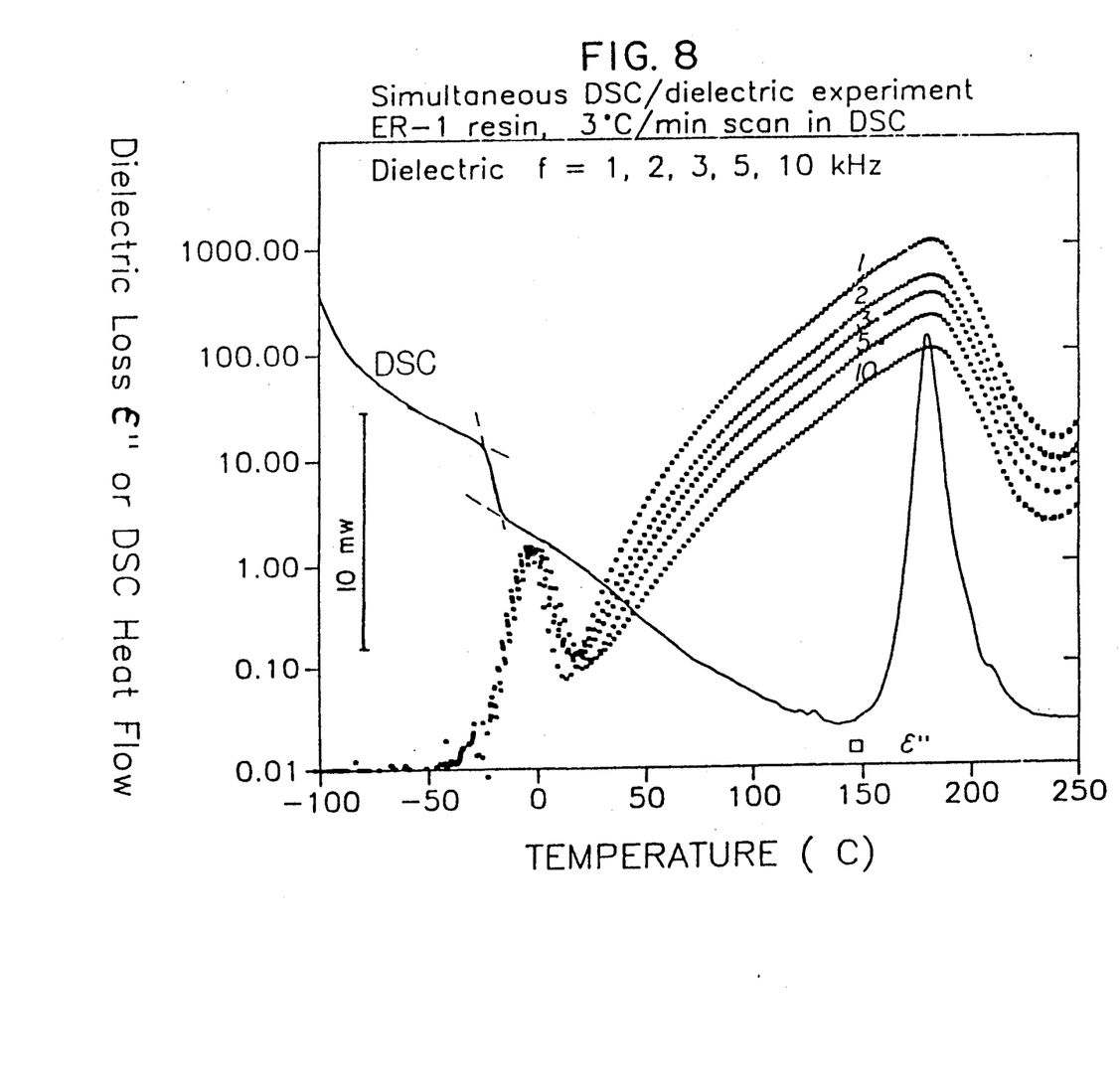
FIG. 8 is a graph showing dielectric loss and DSC heat flow of the ER-1 resin as functions of cell temperature measured from a 3° C./min scan.

FIG. 8 shows the DSC heat flow and the dielectric loss as functions of cell temperature in a 3° C./min scan of a simultaneous DSC-Mirrodielectrometry experiment of ER-1 resin. The low temperature limit of the simultaneous experiment was extended to $-100°$ C. to study the glass transition of the epoxy monomer (EPON-828). The dipolar relaxation process of the epoxy monomer can be studied at low temperatures because the ionic conductivity is very low such that $\epsilon'' \simeq \epsilon''_d$. The glass transition temperature, $T_g$, of EPON-828 measured from the DSC curve is $-24°$ C. The glass transition measured from microdielectrometry, however, is shifted to higher temperatures depending on the excitation frequencies, as is typical of relaxation processes in polymers. Above the glass transition of the EPON-828, the ER-1 resin is in the liquid state and ionic conduction becomes the dominant factor in the dielectric response. A monotonic increase of dielectric losses at all frequencies can be observed in the ionic conduction region from 25° C. to 160° C. The temperature dependence of ionic conduction obeys the Arrhenius law and the activation energy was found to be 22.9 kJ/mol. The curing reaction of epoxy is indicated by the DSC exotherm and by the large decrease of dielectric loss started at about 160° C. Similar to the case of ER-2 resin, the decrease of dielectric loss occurs at higher temperature than the DSC exothermic peak and continues after the end of the exotherm due to the fact that the dielectric response is more sensitive to the local network structure formed near the end point of cure.

Figure 9:
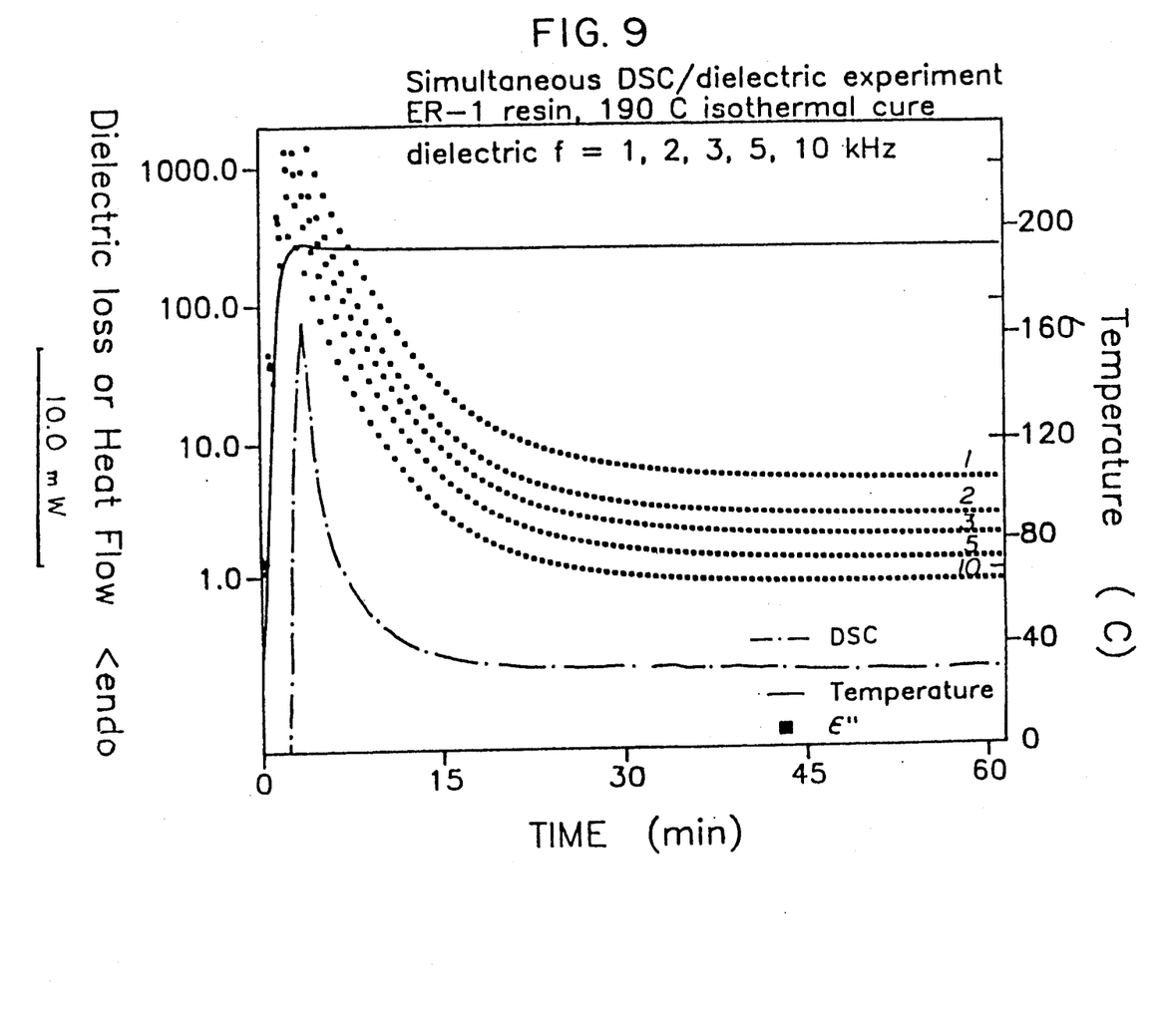
FIG. 9 is a graph showing dielectric loss and DSC heat flow of the ER-1 resin plotted as functions of cure time at 190° C.
Figure 10:
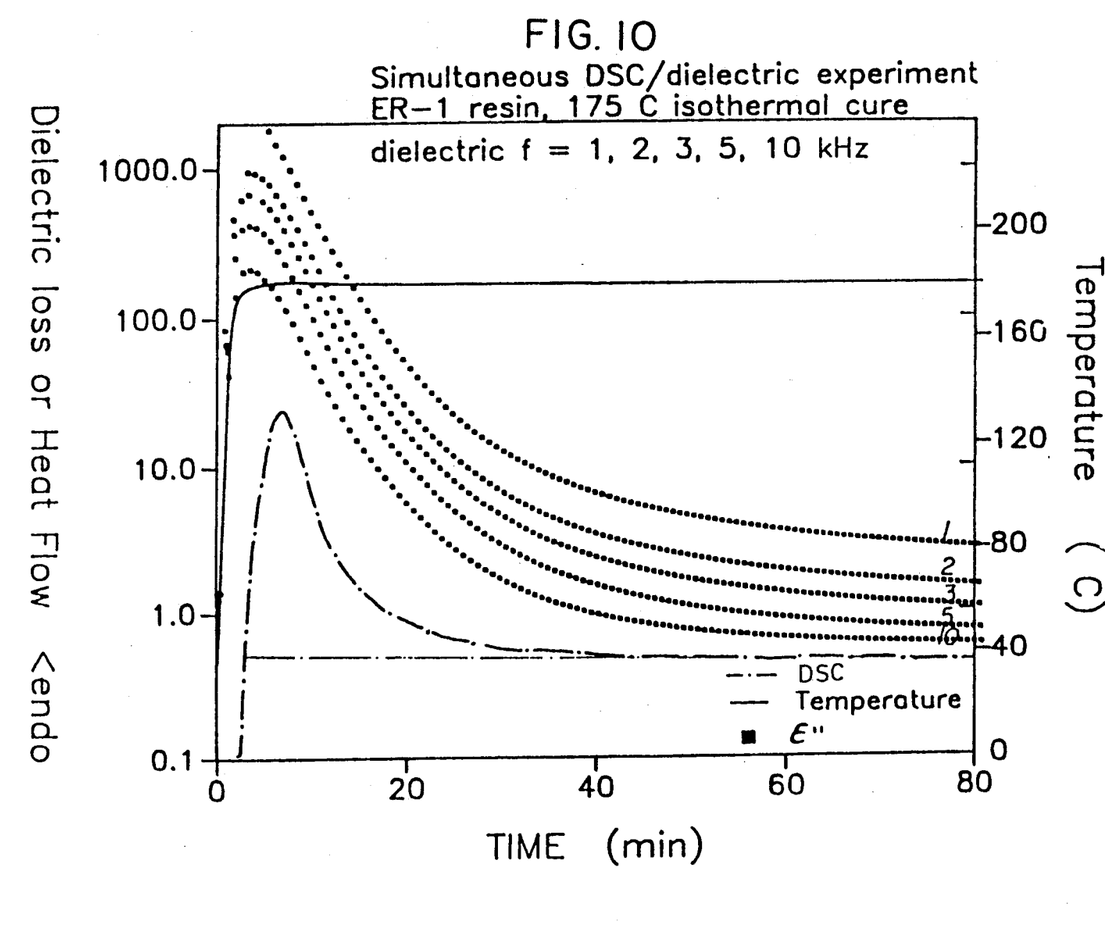
FIG. 10 is a graph showing dielectric loss and DSC heat flow of the ER-1 resin as functions of cure time at 175° C.
Figure 11:
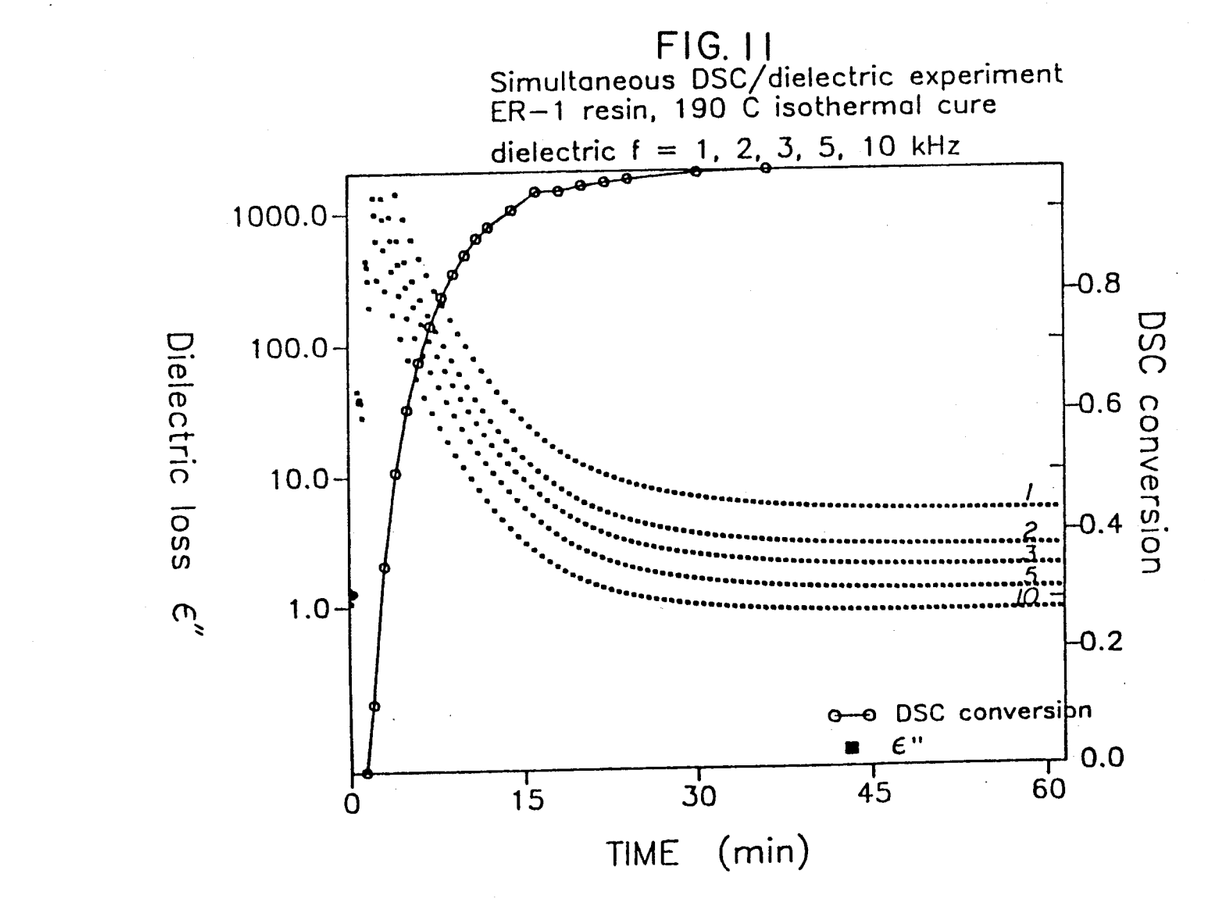
FIG. 11 is a graph showing dielectric loss and extent of reaction (DSC conversion) of the ER-1 resin at 190° C. as functions of cure time.

The simultaneous DSC-Microdielectrometry experiment can also be carried out isothermally to investigate thermoset cure at constant temperatures. FIGS. 9 and 10 illustrate the results of isothermally curing ER-1 resin at 190° and 175° C., respectively. The dielectric loss and the DSC heat flow are plotted as functions of the isothermal cure time. The curing temperature was chosen to be much higher than the glass transition temperature of a fully cured ER-1 resin ($T_g \simeq 130°$ C.) so that the curing reaction would not be limited by vitrification. During an isothermal cure schedule, the dielectric response is only a function of crosslink density related to the degree of conversion, $\alpha$, provided a constant cell temperature is maintained. The cell temperature curve in the figure indicates that a constant temperature condition (with in $\pm 0.1°$ C.) was indeed achieved during the isothermal experiment. Thus, the temperature dependence of the dielectric response was eliminated. The measured dielectric loss, $\epsilon''$, is inversely proportional to the excitation frequency, f, indicating a high ionic conductivity in the curing resin. The DSC heat flow curve shows a strong peak of reaction exotherm at an early stage of reaction. The shape and the area of the reaction exotherm are related to the kinetics and the energetics of the reaction As mentioned in the previous section, the degree of conversion at a given cure time can be calculated by integrating the DSC reaction exotherm to that time By plotting the dielectric loss and the DSC degree of conversion versus time in the same figure, the difference between the dielectric and DSC measurements of cure can be studied. FIG. 11 shows the relationship between the cure time and the dielectric loss, $\epsilon''$, and the DSC degree of conversion, $\alpha$, at 190° C. It is seen from FIG. 11 that there are significant differences in the reaction rates predicted by the DSC degree of conversion, $\alpha$, and by the dielectric loss, $\epsilon''$. The DSC degree of conversion predicts much faster reaction rate at initial stage of cure while the dielectric loss curves show rapid decreases near the completion of reaction. It is also interesting that the two different experimental techniques predict somewhat different end point of the reaction; the end point of cure is 32 minutes determined by the DSC and 46 minutes calculated from ionic viscosity data. The DSC heat flow measurement is less sensitive during late stage of reaction due to a smaller amount of heat released and a limited DSC instrument sensitivity. The dielectric response, however, is more sensitive to the local molecular structure, which is still changing near the end point of cure. Differences in end-point measurements by DSC and dielectrometry as large as 25% have been observed from experiments conducted separately. The reported difference is primarily due to two factors: 1, effect of sample preparation and thermal history of the DSC and dielectric specimens, and 2, poor temperature control during late stage of thermoset cure. In a simultaneous experiment with well maintained isothermal conditions, however, the delayed end-point of cure reflected in the dielectric loss curves can only be attributed to the slow crosslinking reactions, detectable only by dielectric measurement, still occurring near the completion of cure.

Figure 12:
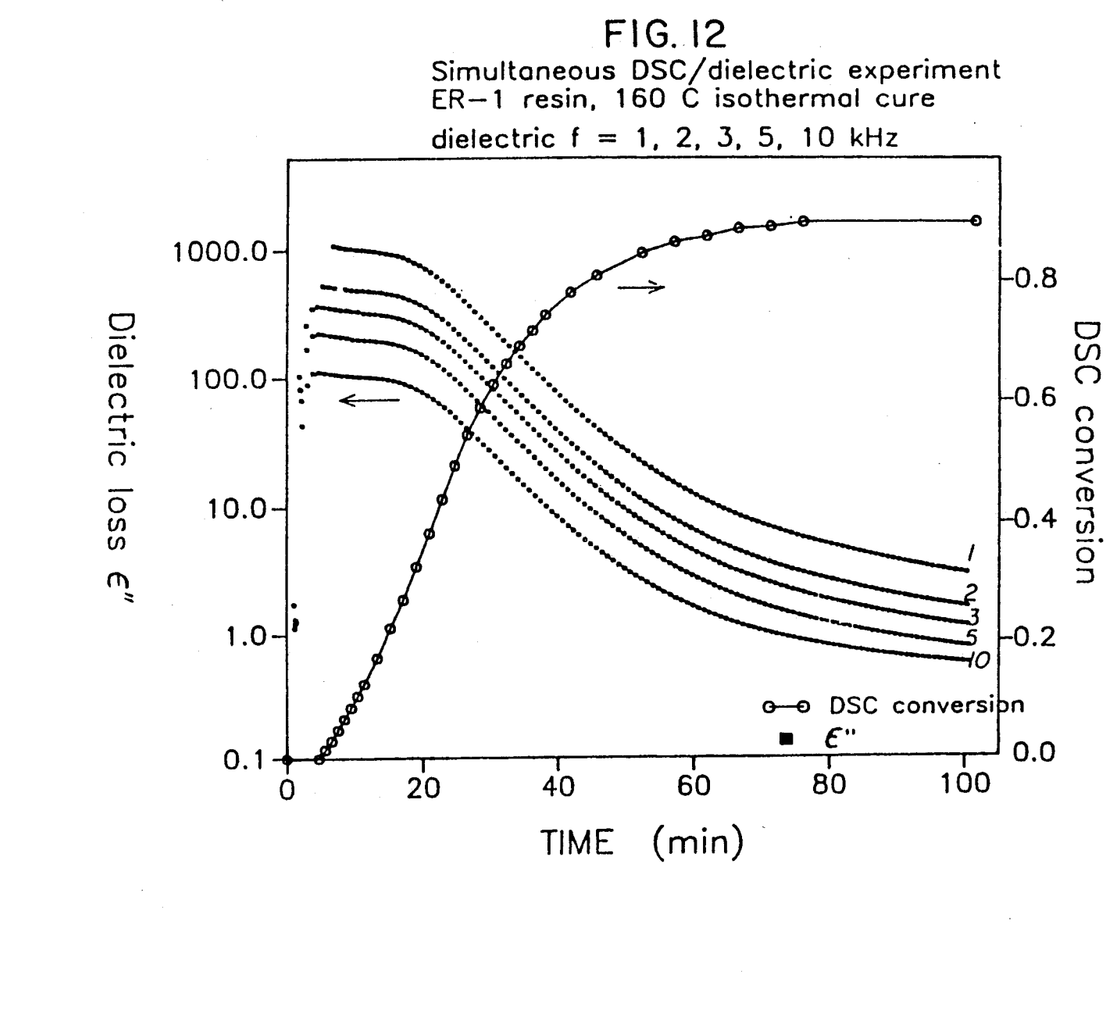
FIG. 12 is a graph showing dielectric loss and extent of reaction (DSC conversion) as functions of cure time of the ER-1 resin cured isothermally at 160° C.

The curing reaction of ER-1 proceeded very slowly and did not reach completion at the lowest cure temperature studied (160° C.), according to the DSC heat of reaction and the dielectric responses shown in FIG. 12. At this temperature, the curing reaction of the epoxy/dicyandiamide resin proceed very slowly. The measured DSC conversion at 160° C. reached a plateau of 89% completion after 75 min. of reaction time. The dielectric loss curves at all frequencies, however, are still decreasing at that time due to a slow increase in the crosslink density during late stage of cue. The incomplete cure of ER-1 resin at 160° C. can be attributed to two factors: a slower reaction rate at lower temperatures and an incomplete mixing of the melted dicyandiamide curative at this temperature.

Figure 13:
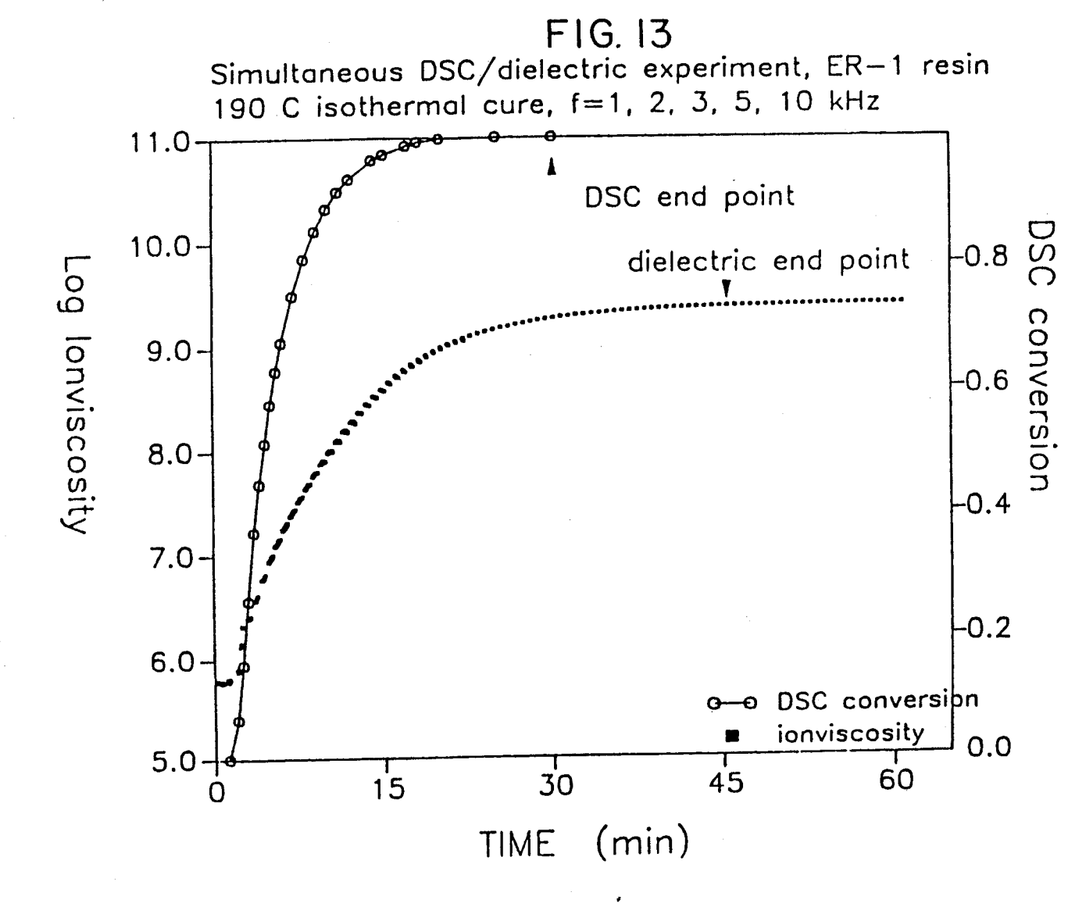
FIG. 13 is a graph showing ionic viscosity and extent of reaction (DSC conversion) of the ER-1 resin as functions reaction time at 175° C.
Figure 14:
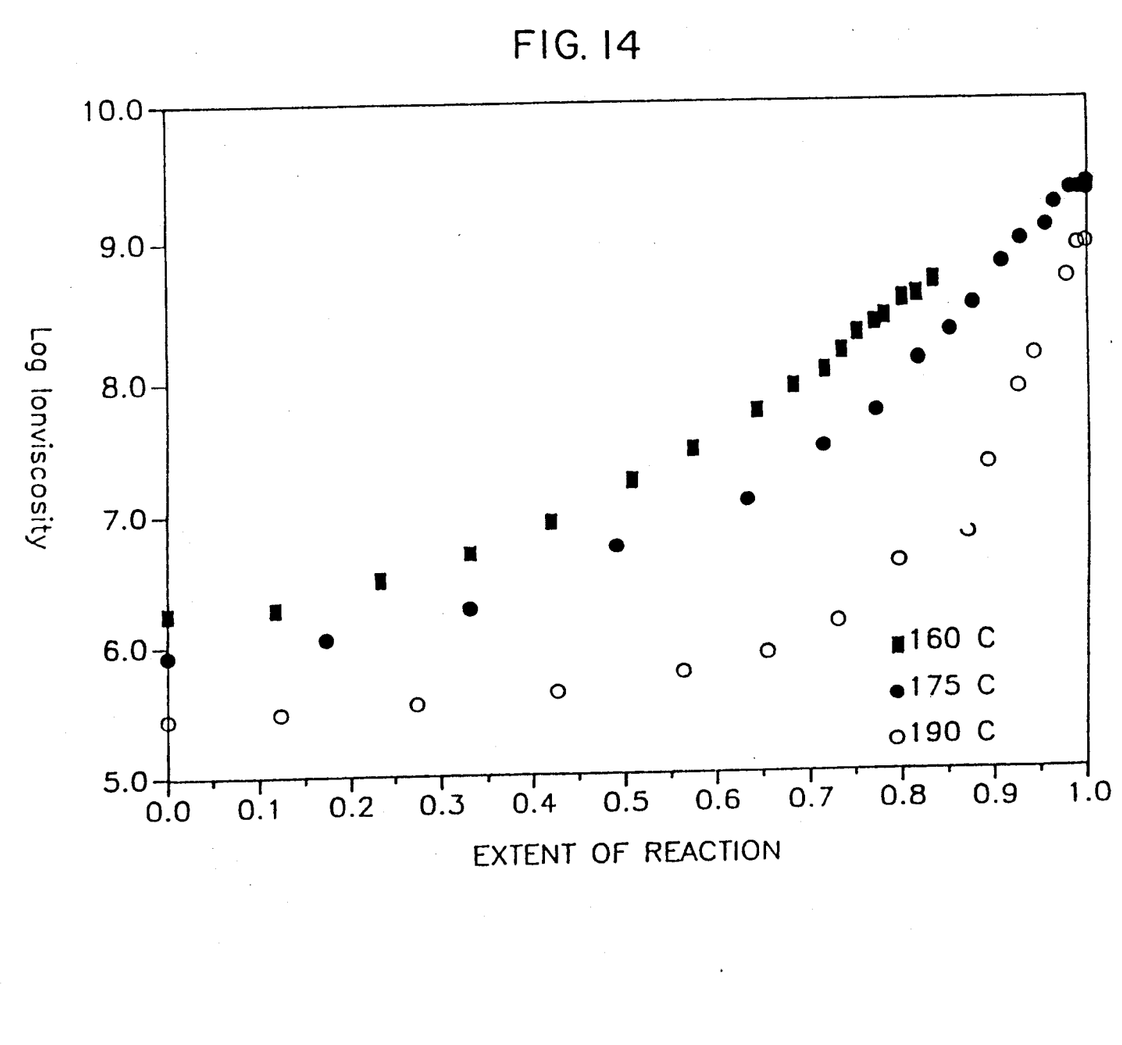
FIG. 14 is a graph showing ionic viscosity as a function of extent of reaction (DSC conversion) of ER-1 resin at different isothermal cure temperatures.

The frequency dependence of the dielectric loss, $\epsilon''$, of an isothermal cure experiment can be eliminated by plotting the ionic viscosity, $\eta_i$, provided the ionic conduction dominates the dielectric response. FIG. 13 illustrates the calculated ionic viscosity and DSC conversion as functions of cure time at 175° C. It is seen that ionic viscosity shows a delayed response as compared to the DSC prediction of end point. FIG. 13 also indicates a non-linear relationship between DSC conversion and ionic viscosity. FIG. 14 shows the relationship between ionic viscosity, $\eta_i$, and DSC degree of conversion, $\alpha$, of isothermal cure at three different temperatures. The relationship is non-linear and the ionic viscosity changes significantly from about 65% conversion to the end point of cure. The non-linear effect becomes more significant at higher curing temperatures due to the difference in the network structures formed at different temperatures.

Figure 15:
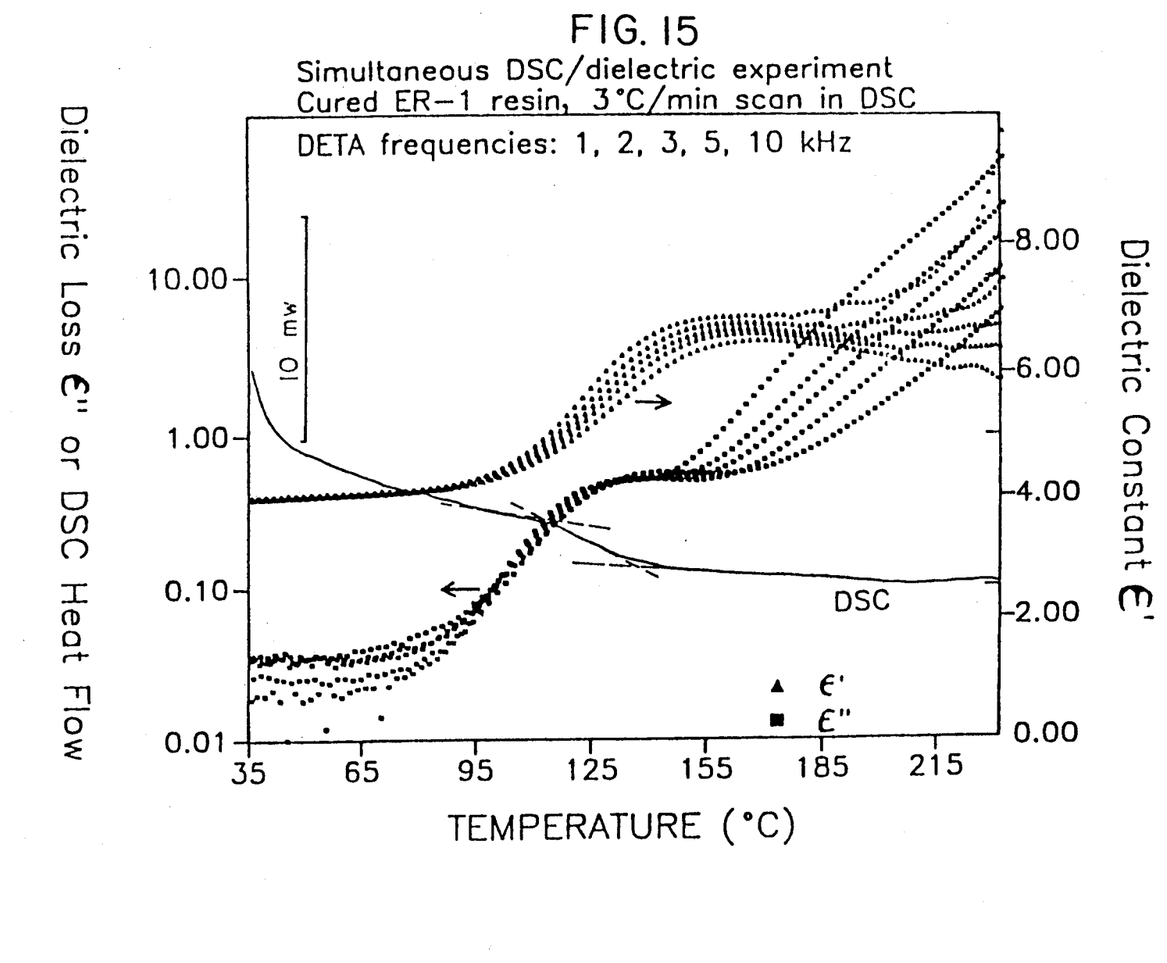
FIG. 15 is a graph showing dielectric constant, dielectric loss, and DSC heat flow of a cured ER-1 resin as functions of cell temperature in a 3° C./min scan.

FIG. 15 shows a simultaneous DSC-Microdielectrometry scan of a cured ER-1 sample from 0° C. to 200° C. at 3° C./min. The dielectric constant, $\epsilon'$, and the dielectric loss, $\epsilon''$, of the cured sample contain both dipolar and ionic contributions. The dipolar relaxation is indicated by the frequency dependent $\epsilon''$ peaks attributed to the glass transition temperature at around 130° C. The ionic conduction in this sample is indicated by the rapid rise of $\epsilon''$ at all testing frequencies at higher temperatures. The ionic viscosity, $\eta_i$, was calculated from the high temperature dielectric loss data. The temperature dependence of the ionic viscosity could be represented by the Arrhenius law and the activation energy of ionic conduction in the cured ER-1 resin can be estimated. It was found the activation energy of ionic conduction in the crosslinked ER-1 resin is about 4 times higher (107.9 kJ/mol) than that of liquid resin (25.2 kJ/mol). Such a high activation energy can be explained by the restrictions of the crosslinked network in the cured resin to the ionic diffusion process. The dielectric response of a fully crosslinked resin over a wide temperature range are useful for mapping the end point of cure of that resin.

The present invention has been described with reference to certain preferred embodiments and those skilled in the art, in view of the present disclosure, will appreciate that numerous alternative embodiments of the invention are within the scope of the following claims. Accordingly, any and all modifications, variations or equivalent arrangements, which may occur to those skilled in the art, should be considered to be within the scope of the invention as defined in the appended claims.

What is claimed is:

1. A device for testing properties of materials, comprising:
    means defining a sample cell;
    and means for simultaneously measuring dielectric and thermal properties of a material in the sample cell, said thermal properties including at least heat capacity, and said means for measuring dielectric properties including at least one of measuring dielectric constant and dielectric loss of said material.

2. A device according to claim 1, further comprising means for applying heat to said sample cell and means for measuring energy input to said sample cell.

3. A device according to claim 1, further comprising means for measuring a current passed through said sample cell.

4. A device according to claim 1, further comprising:
    means for measuring the temperature of said sample cell;
    means for measuring a current passed through the material in said sample cell;
    means for applying heat to said sample cell; and
    means for measuring energy input to said sample cell.

5. A device according to claim 1, further comprising means for applying a voltage to said sample cell.

6. A sample cell for use in simultaneous microdielectrometry and differential scanning calorimetery measurement, comprising:
    means for containing a sample therein;
    means for sensing and transmitting a signal representative of the heat capacity and heat of melting of the sample; and
    means for sensing and transmitting a signal representative of dielectric properties of the sample, whereby simultaneous measurement of dielectric and calorimetric properties of the sample can be determined.

7. A sample cell according to claim 6, wherein said means for sensing and transmitting a signal representative of dielectric properties includes a sensor disposed in said sample cell.

8. A sample cell according to claim 6, wherein said means for containing includes a base member and a cover member and said means for sensing and transmitting a signal representative of dielectric properties of the sample, includes a sensor disposed in said sample cell.

9. A sample cell according to claim 8, wherein said means for sensing and transmitting a signal representative of dielectric properties of the sample is disposed adjacent to said base member.

10. A sample cell according to claim 8, wherein said means for sensing and transmitting a signal representative of dielectric properties of the sample is disposed adjacent to said cover member.

11. A sample cell according to claim 8, wherein said means for sensing and transmitting a signal representative of dielectric properties of the sample is disposed on top of the sample.

12. A sample cell according to claim 8, wherein said means for sensing and transmitting a signal representative of dielectric properties of the sample for simultaneous measurement includes a cable attached to said sensor.

13. A sample cell according to claim 12, wherein said cable is a Kapton ribbon cable.

14. A method for simultaneously measuring the dielectric and thermal properties of a material, comprising the steps of:
    applying a voltage to a material;
    simultaneously measuring the temperature of the material; and
    simultaneously measuring heat capacity and heat of melting of the material.

15. A method according to claim 14, wherein said method further comprises the step of:
    heating the material over a temperature range and repeating said measurement.

* * * * *